United States Patent
Kasagi et al.

(10) Patent No.: US 9,296,814 B2
(45) Date of Patent: Mar. 29, 2016

(54) ANTIBODY AGAINST HUMAN TSH AND CANINE TSH

(75) Inventors: Noriyuki Kasagi, Ashigarakami-gun (JP); Yuya Watanabe, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 625 days.

(21) Appl. No.: 13/592,802

(22) Filed: Aug. 23, 2012

(65) Prior Publication Data

US 2013/0052666 A1    Feb. 28, 2013

(30) Foreign Application Priority Data

Aug. 24, 2011   (JP) .................................. 2011-182204

(51) Int. Cl.
*C07K 16/26* (2006.01)

(52) U.S. Cl.
CPC ............. *C07K 16/26* (2013.01); *C07K 2317/33* (2013.01); *C07K 2317/92* (2013.01)

(58) Field of Classification Search
None
See application file for complete search history.

(56) References Cited

U.S. PATENT DOCUMENTS

| 4,692,404 A | 9/1987 | Ashihara et al. |
| 4,757,001 A | 7/1988 | Ashihara et al. |
| 5,447,846 A | 9/1995 | Shinoki et al. |
| 2009/0087923 A1 | 4/2009 | Muraya et al. |

FOREIGN PATENT DOCUMENTS

| EP | 0212522 | 3/1987 |
| EP | 2336158 | 6/2011 |
| JP | 60-108756 A | 6/1985 |
| JP | 60-171460 A | 9/1985 |
| JP | 60-171461 A | 9/1985 |
| JP | 6238362 | 2/1987 |
| JP | 07072147 | 3/1995 |
| JP | 3151080 B2 | 1/2001 |
| JP | 2008249361 A | 10/2008 |
| JP | 2009-85703 A | 4/2009 |
| JP | 2010512744 | 4/2010 |
| JP | 2010261791 | 11/2010 |
| JP | 2011128110 | 6/2011 |
| WO | 2008076255 | 6/2008 |

OTHER PUBLICATIONS

Communication for EP Application No. 12 18 1706 dated Jan. 14, 2013, along with a European Search Report dated Dec. 18, 2012.
Office Action for Japanese Application No. 2011-182204 dated Apr. 30, 2013.

*Primary Examiner* — Galina Yakovleva
*Assistant Examiner* — Andrea S Grossman
(74) *Attorney, Agent, or Firm* — Sughrue Mion, PLLC

(57) ABSTRACT

It is an object of the present invention to provide an antibody that recognizes a canine TSH and binds thereto, without obtaining a large amount of canine TSH antigen. The present invention provides a monoclonal antibody produced by a hybridoma having Accession No. FERM BP-11490.

8 Claims, 7 Drawing Sheets

ANTIBODY AGAINST HUMAN TSH AND CANINE TSH

TECHNICAL FIELD

The present invention relates to an antibody against human TSH and canine TSH, a hybridoma that produces the aforementioned antibody, and a reagent and a measurement method, in which the aforementioned antibody is used.

BACKGROUND ART

Hormone is a substance, which is present in a trace amount in the blood of a living body and governs various physiological activities. Thyroid stimulating hormone (TSH), which is one type of thyroid hormone, is often measured in clinical sites in order to determine and/or grasp thyroid function. In a normal state, the thyroid gland is stimulated by thyroid stimulating hormone (TSH), and as a result, thyroxine (T4) is secreted. However, when thyroid function is decreased as in the case of Hashimoto's disease, T4 is not secreted although TSH is secreted. Accordingly, when a subject is suspected to have hypothyreosis, the subject's TSH level in blood needs to be measured.

However, since hormone such as TSH is present only in a trace amount in the blood, a reagent and an apparatus, which are capable of high sensitivity quantification, are required. With regard to immunodiagnostic reagents using an antigen-antibody reaction, examples of a method not involving a labeling reaction, namely, a non-labeling method, include: immunodiffusion, immunonephelometry and nephelometry, which utilize a precipitation reaction; and erythrocyte agglutination and a latex method, which utilize an agglutination reaction. On the other hand, examples of a method involving a labeling reaction, which is currently used, include enzyme immunoassay (EIA method), radioimmunoassay (RIA method), fluorescence immunoassay (FIA method), chemiluminescence immunoassay (CLIA method), and bioluminescence immunoassay (BLIA method). These methods are applied depending on the type or property of a substance to be labeled. As a method for measuring TSH, for example, JP Patent Publication (Kokai) No. 2009-85703 A describes a method for measuring TSH, which comprises using a commercially available antibody against human TSH, allowing TSH to come into contact with a carrier to which the aforementioned anti-TSH antibody has been bound, and then measuring an agglutination generated as a result of the aforementioned contact, wherein the method is characterized in that multiple types of anti-TSH antibodies, which recognize different TSH epitopes, are independently supported on individual carriers, and the thus obtained TSH antibody-supported carriers are then each allowed to come into contact with an analyte containing TSH on a time difference basis.

For the above-described immunodiagnosis of TSH, a TSH antibody is required. However, since a canine TSH (hereinafter also referred to as "cTSH") antigen is present only in a trace amount in a living body, it is difficult to ensure a sufficient amount of canine TSH antigen used as an immunogen in the production of a canine TSH antibody. Moreover, at present, such a canine TSH antibody is not commercially available. Furthermore, since it is also difficult to construct an expression system of a recombinant canine TSH protein, it is difficult to obtain a large amount of canine TSH protein. As described above, since it is not possible to obtain a large amount of canine TSH protein, ordinary immunization cannot be conducted. As such, it has been difficult to produce an anti-canine TSH antibody.

DISCLOSURE OF INVENTION

It is an object of the present invention to provide an antibody that recognizes a canine TSH and binds thereto, without obtaining a large amount of canine TSH antigen. It is another object of the present invention to provide a hybridoma that produces the above-described antibody, an immunoanalytical reagent comprising the above-described antibody, and a method for measuring canine TSH using the above-described antibody.

As a result of intensive studies directed towards achieving the aforementioned objects, the present inventors have succeeded in producing an anti-canine TSH antibody by performing immunization utilizing human TSH as an immunogen, thereby completing the present invention.

The present invention provides a monoclonal antibody which binds both canine TSH and human TSH, or a fragment thereof.

Preferably, the monoclonal antibody of the present invention or a fragment thereof has a dissociation constant of $10^{-7}$ M or less to canine TSH and human TSH. It is because, if such requirement is satisfied, the antibody of the present invention can be used for the analysis of both canine TSH and human TSH.

Preferably, the subclass of the monoclonal antibody of the present invention is IgG1, 2a, 2b, or 3.

Preferably, the monoclonal antibody of the present invention or a fragment thereof is obtained by administering human THS as an antigen to immunization animal and selecting an antibody having a reactivity with canine TSH among from the generated antibodies.

Preferably, the monoclonal antibody of the present invention is an monoclonal antibody which is produced by a hybridoma having Accession No. FERM BP-11489, FERM P-22074, FERM P-22075, FERM BP-11490, or FERM P-22077. Particularly, the monoclonal antibody of the present invention is an monoclonal antibody which is produced by a hybridoma having Accession No. FERM BP-11490.

The present invention further provides a hybridoma which produces the antibody of the present invention.

Preferably, there is provided a hybridoma having Accession No. FERM BP-11489, FERM P-22074, FERM P-22075, FERM BP-11490, or FERM P-22077. Particularly, there is provided a hybridoma having Accession No. FERM BP-11490.

The present invention further provides an immunoanalytical reagent which comprises the antibody of the present invention or a fragment thereof.

The present invention further provides an immunoanalytical reagent which comprises the antibody of the present invention or a fragment thereof, wherein the antibody or a fragment thereof is labeled with latex particles containing a dye or a fluorescent dye.

The present invention further provides an immunoanalytical reagent which comprises the antibody of the present invention or a fragment thereof, wherein the antibody or a fragment thereof is labeled with an enzyme.

The present invention further provides an immunoanalytical reagent consisting of a combination of a labeled antibody prepared by labeling a monoclonal antibody produced by a hybridoma having Accession No. FERM P-22075 or FERM BP-11490 with latex particles containing a dye or a fluorescent dye, with a monoclonal antibody produced by a hybridoma having Accession No. FERM BP-11489, FERM P-22074 or FERM P-22077. Particularly, there is provided an immunoanalytical reagent consisting of a combination of a labeled antibody prepared by labeling a monoclonal antibody produced by a hybridoma having Accession No. FERM BP-11490 with latex particles containing a dye or a fluorescent dye, with a monoclonal antibody produced by a hybridoma having Accession No. FERM BP-11489, FERM P-22074 or FERM P-22077.

Preferably, the immunoanalytical reagent of the present invention is used in the measurement of canine TSH.

The present invention further provides a method for measuring human TSH or canine TSH in a sample, which comprises allowing a sample to come into contact with the immunoanalytical reagent for canine TSH measurement of the present invention.

Effect of the Present Invention

The antibody of the present invention is able to bind to human TSH and canine TSH. Since the antibody of the present invention is produced using human TSH as an immunogen, it can be produced without requiring a large amount of canine TSH antigen.

DESCRIPTION OF EMBODIMENTS

Figure 1:
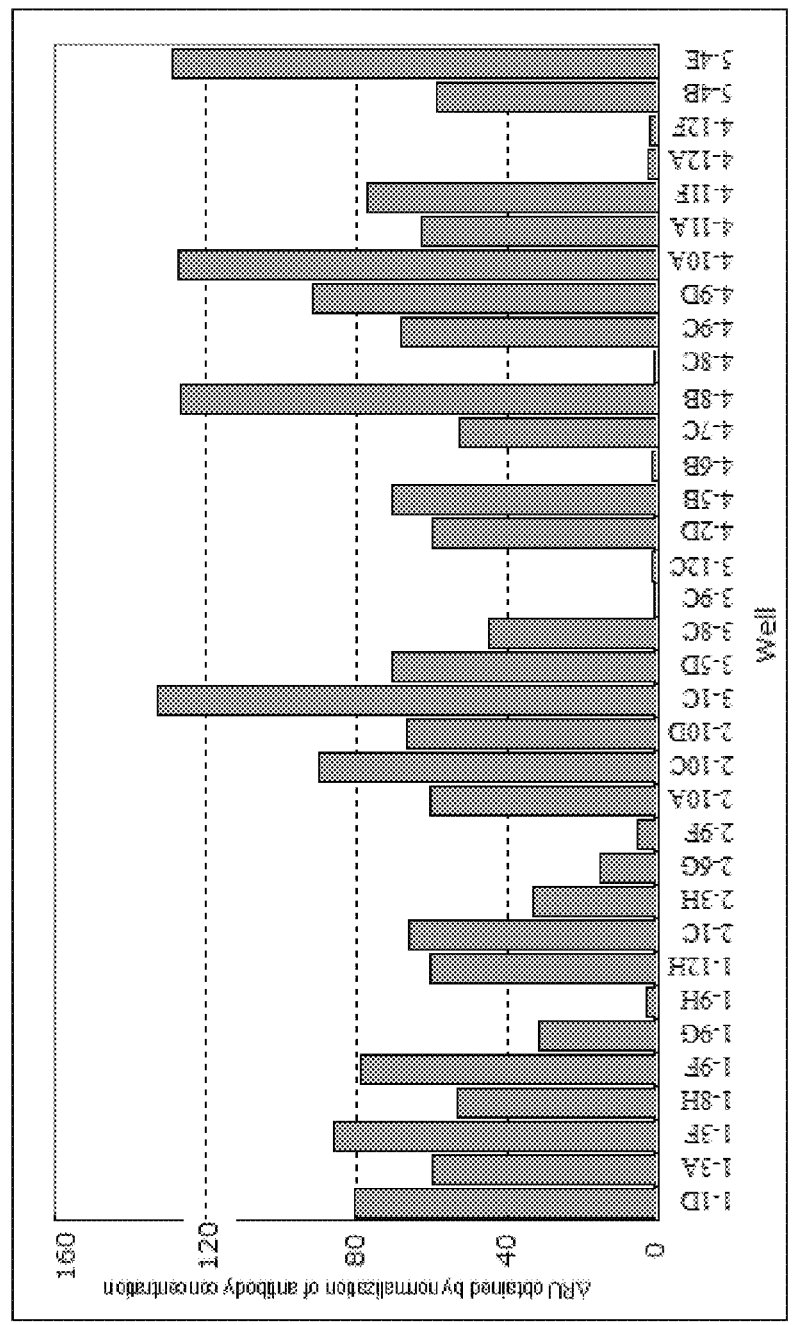
FIG. 1 shows the reactivity of the obtained antibody with a human TSH antigen.

Hereinafter, the present invention will be more specifically described.

The antibody of the present invention is a monoclonal antibody that binds to canine TSH and human TSH. It is to be noted that the term "antibody" is used in the present invention to mean not only an antibody molecule as a whole, but also a fragment thereof (for example, Fab, F(ab')$_2$, and Fab' fragments).

The antibody of the present invention can be preferably obtained by selecting an antibody having reactivity with both canine TSH and human TSH, from among antibodies produced by administering human TSH as an antigen to animals to be immunized.

A monoclonal antibody can be obtained by the following method. Specifically, an antigen is injected into the abdominal cavity or the like several times together with an adjuvant, and spleen cells are then collected. Thereafter, using polyethylene glycol or the like, the collected cells are fused with mouse myeloma cells. Thereafter, antibody-producing cells are cloned from the fused cells, and they are then allowed to proliferate as monoclone cells. The thus proliferating cells are further injected into the abdominal cavity of a mouse to obtain ascites and serum that contain a monoclonal antibody. More specifically, a monoclonal antibody can be obtained as follows.

First, human TSH is used as an antigen, and it is administered to a mammal such as a rat, a mouse, or a rabbit. The dose of the antigen per animal is 0.1 to 100 mg when an adjuvant is not used. It is 1 to 2000 µg when an adjuvant is used. Examples of such an adjuvant include a Freund's complete adjuvant (FCA), a Freund's incomplete adjuvant (FIA), and an aluminum hydroxide adjuvant. Immunization is mainly carried out by injecting an antigen into the vein, subcutis, or abdominal cavity. The immunization interval is not particularly limited. Immunization is carried out at intervals of several days to several weeks, and preferably 2 to 5 weeks, 1 to 10 times, and preferably 2 to 5 times. Thereafter, antibody-producing cells are collected 1 to 60 days, and preferably 1 to 14 days after the final immunization. Such antibody-producing cells include spleen cells, lymph node cells, peripheral blood cells, and others. Spleen cells or regional lymph node cells are preferable.

To obtain cell fusion hybridomas, cell fusion is carried out by fusing antibody-producing cells with myeloma cells. As myeloma cells to be fused with antibody-producing cells, generally available cell lines established from animals such as mice can be used. Used cell lines are preferably those, which do not survive in a HAT selective medium (containing hypoxanthine, aminopterin, and thymidine) in the state of unfused cells, and which survive only in a state in which they are fused with antibody-producing cells. Myeloma cells include mouse myeloma cell lines such as P3×63-Ag.8.U1(P3U1) and NS-I.

Subsequently, the aforementioned myeloma cells and antibody-producing cells are fused. In cell fusion, antibody-producing cells ($1 \times 10^6$ to $1 \times 10^7$ cells/ml) are mixed with myeloma cells ($2 \times 10^5$ to $2 \times 10^6$ cells/ml) in an animal cell culture medium containing no serum, such as DMEM or RPMI-1640 medium (the cell ratio between the antibody-producing cells and the myeloma cells is preferably 5:1), and a fusion is carried out in the presence of a cell fusion promoter. As such a cell fusion promoter, polyethylene glycol having a mean molecular weight of 1000 to 6000 daltons or the like can be used. Moreover, antibody-producing cells can also be fused with myeloma cells using a commercially available cell fusion apparatus that utilizes electrical stimulation (for example, electroporation).

Hybridomas of interest are selected from the cells that have undergone cell fusion. As a selection method, a cell suspension is diluted, as appropriate, with a fetal bovine serum-containing RPMI-1640 medium or the like, and it is then dispersed on a microtiter plate in a concentration of approximately $3 \times 10^5$ cells/well. Thereafter, a selective medium is added to each well, and a culture is then carried out while appropriately exchanging the medium with a fresh one. As a result, cells that grow approximately 14 days after initiation of the culture with a selection medium can be obtained as hybridomas.

Subsequently, screening is carried out to examine the presence or absence of an antibody of interest in a culture supernatant of such growing hybridomas. The screening of hybridomas may be carried out by an ordinary method. Thus, the type of the screening method is not particularly limited. For example, an aliquot of a culture supernatant contained in a well in which hybridomas have grown may be collected, and it may be then screened by an enzyme immunoassay (ELISA, etc.), a radioimmunoassay, or the like.

The cloning of the fused cells is carried out by a limiting dilution method or the like, and hybridomas can be finally established as monoclonal antibody-producing cells.

As a method of collecting monoclonal antibodies from the established hybridomas, a common cell culture method, an ascites formation method, and the like can be adopted. In the cell culture method, hybridomas are cultured in an animal cell culture medium such as a 10% fetal bovine serum-containing RPMI-1640 medium, an MEM medium, or a serum free medium, under general culture conditions (for example, 37° C., 5% $CO_2$ concentration) for 7 to 14 days. Thereafter, antibodies are obtained from a culture supernatant.

In the case of the ascites formation method, approximately $1 \times 10^7$ hybridomas are administered into the abdominal cavity of an animal of the same species as an mammal from which myeloma cells are derived, so that large quantities of hybridomas are allowed to proliferate therein. One or two weeks later, ascites is collected. When it is necessary to purify antibodies in the aforementioned method of collecting antibodies, the collected antibodies can be purified by appropriately selecting a method from known purification methods such as ammonium sulfate fractionation, ion exchange chromatography, gel filtration, and affinity chromatography (protein A-aragose, etc.), or by applying these purification methods in combination.

Examples of an antibody subclass include IgG1, IgG2a, IgG2b, and IgG3. The subclass used in the present invention is IgG1 exhibiting good antibody fragmentation efficiency when an enzyme-antibody complex is produced. The obtained IgG1 may be converted to $F(ab')_2$ by eliminating its Fc portion with protease such as activated papain or pepsin. The $F(ab')_2$ may be further reduced, so that it can be induce to a Fab' fragment.

In a preferred embodiment, a Fab' fragment is used as a monoclonal antibody. An intact antibody (IgG) has Fab (an antigen-binding site) and Fc (a complement-binding site). When an intact antibody is allowed to bind to an enzyme, and the obtained product is used as an enzyme-labeled antibody, if a sample is a blood sample, a complement component in the blood may bind to an Fc portion, thereby causing steric hindrance and inhibiting enzyme activity. Even in a case in which a sample is not a blood sample, since such Fc portions are non-specifically adsorbed on the wall of a reactor, or the pores or the surfaces of internal voids of a porous member that constitute immune reaction layer, the activity of an enzyme-labeled antibody becomes apparently low, and this causes noise during the measurement. To eliminate such noise, it is desired to use an Fab', $F(ab')_2$, or Fab fragment containing no Fc portions as an antibody. Of these, an Fab' fragment having a free SH group is most preferably used as an antibody, in terms of convenience for binding to enzyme.

The aforementioned monoclonal antibody of the present invention, a latex reagent labeled with the aforementioned monoclonal antibody or a fragment thereof, and the aforementioned monoclonal antibody or a fragment thereof, which is labeled with an enzyme (for example, *Bacillus subtilis* α-amylase, etc.), can be used as immunoanalytical reagents (preferably, as immunoanalytical reagents for measuring canine TSH).

Such an enzyme used as a labeling substance can be selected, while taking into account a combination of the enzyme with an enzyme substrate used in the subsequent enzyme reaction. In the present invention, reactivity with an enzyme reacting with an enzyme substrate is suppressed by steric hindrance caused by formation of a matrix-like structure consisting of an enzyme, an antibody, and an antigen. Thus, as a combination of an enzyme with a substrate, a system for easily detecting the influence of such steric hindrance is preferably selected. That is to say, in terms of sensitivity, a relatively high-molecular-weight enzyme substrate is preferable. For example, a substrate with a molecular weight of approximately 20,000 or more, and more preferably of approximately 100,000 or more, is used. Such a substrate that binds to amylase is starch; such a substrate that binds to cellulase is cellulose; such substrates that bind to protease are proteins such as gelatin or hemocyanin; and such substrates that bind to lipase are various types of lipids. JP Patent Publication (Kokai) Nos. 60-108756 A (1985), 60-171461 A (1985), and 60-171460 A (1985) disclose in detail selection of the aforementioned enzyme and substrate. Among the aforementioned combinations of enzymes with substrates, amylase whose enzyme substrate is starch is preferable. In addition, water-insoluble substrates are particularly preferably used because the steric hindrance caused by a matrix-like structure consisting of an enzyme, an antibody, and an antigen is prominently manifested.

Examples of amylase include α-amylase, β-amylase, and glucoamylase. Amylase that is not substantially contained in a sample is preferable in terms of noise prevention. The origin of such amylase varies widely from animals (saliva, pancreatic juice, etc.) and plants to microorganisms. Thus, when the body fluid, blood, or the like of a human or animal is analyzed, it is preferable not to use amylase derived from such a higher animal.

Examples of amylases derived from microorganisms or plants include: glucoamylases derived from *Aspergillus* sp., *Rhizopus* sp., *Saccharomyces* sp., etc.; β-amylases derived from barley malt, wheat, soybean, etc.; and α-amylases derived from *Bacillus Subtilis, Streptomyces griseus, Pseudomonas stutzeri, Thermoactiomyces vulgaris*, etc. Of these, α-amylase derived from *Bacillus Subtilis* is most preferable because it has high liquefying power and excellent heat stability.

These enzymes are preferably not affected by interfering factors existing in all analytes. In addition, it is preferable that no competitive enzymes of the same species be present in an analyte. If an enzyme of the sample species as a labeling enzyme were contained in an analyte, an enzyme inhibitor might be used. The level of such an enzyme inhibitor to inhibit an enzyme contained in an analyte may be greater than the level thereof to inhibit the activity of a labeling enzyme. An enzyme inhibitor that completely deactivates an enzyme contained in an analyte but that does not inhibit at all a labeling enzyme is most preferable. From a practical viewpoint, however, it is sufficient if a blank value is not increased by such an enzyme inhibitor during the measurement. Thus, it is acceptable even if an enzyme inhibitor is deactivated and the activity of enzyme contained in a sample is recovered after the measurement. The type of such an enzyme inhibitor is not particularly limited, as long as it does not inhibit the enzyme of an enzyme-labeled antibody. It is acceptable even if such an enzyme inhibitor inhibits an enzyme in a free state. As such an enzyme inhibitor, that having the aforementioned specificity may be selected from known enzyme inhibitors and may be used. Otherwise, an antibody reacting with problematic enzyme contained in an analyte may be produced, and it may be used as an enzyme inhibitor.

When α-amylase is used as an enzyme, carboxymethylated starch, starch, amylose, amylopectin, or the like may be used as a substrate. In particular, if water-insoluble starch or the like is used, an enzyme reaction takes place on the surface of a substrate particle, namely, on the interface between solid and liquid. As a result, the influence of steric hindrance due to an antibody-antigen bond upon enzyme activity appears significantly. Thus, the use of such water-insoluble starch is preferable in terms of sensitivity. Moreover, water-insoluble dye starch may be used to detect dye (pigment) adhering to soluble amylose as an enzyme decomposed product. As such water-insoluble blue starch polymer, a commercially available product such as Neo-Amylase (manufactured by Daiichi Kagaku Yakuhin Co.) can be used.

A method of binding an enzyme with an antibody can be carried out utilizing the functional groups of the two substances (an amino group, a carboxyl group, a thiol group, etc.). Representative binding methods include a glutaraldehyde method, a periodic acid method, a pyridyl disulfide method, and a maleimide-succinimide method. However, examples of such a binding method are not limited thereto. In addition to the aforementioned methods, a method may be selected, as appropriate, from those described in publications such as "Method in Immunology and Immunochemistry," Vol. 1, C. A. Williams, M. W. Chase, Academic Press, 1967, or "*Koso Meneki Sokutei Ho* (Enzyme Immunoassay)" edited by Ishikawa, Kawai, and Miyai, Igaku-Shoin, Ltd., 1978, and it may be then used. Among these binding methods, a maleimide-succinimide method comprising binding a thiol group of an antibody hinge portion to an amino group of enzyme via crosslinkage is superior in terms of good reaction efficiency and ability to maintain antibody activity.

In such a maleimide-succinimide method, an enzyme is allowed to bind to Fab', for example, as follows. First, an amino group of the enzyme is maleimidated with a maleimide-succinimide reagent. The resultant is purified by gel filtration, and it is then combined with an antibody having a thiol group (Fab'). In this complex formation, two or more types of antibodies having different epitopes (Fab') may be used in combination. In such a case, such antibody fragments are subjected to a binding reaction with each other. This complex formation reaction is preferably carried out using 3 to 7 moles of antibodies with respect to 1 mole of enzyme. When Fab' (molecular weight: approximately 50,000) is used as an antibody and α-amylase (molecular weight: approximately 50,000) is used as an enzyme, a binding reaction is preferably carried out using 1/3 to 1/7 by weight of α-amylase with respect to the total weight of Fab'. This binding reaction is generally carried out at a temperature from 4° C. to room temperature.

The generated enzyme-antibody complex (enzyme-labeled antibody) is purified by gel filtration, and as necessary, it is dried by freeze-drying. The binding ratio between an enzyme and each antibody is not limited to 1:1, and any given ratio can be applied depending on purposes. Since an enzyme generally has a large number of amino groups, multiple maleimide groups are introduced, and multiple antibody molecules are introduced into a single enzyme molecule. Since at least one antibody molecule should bind to one enzyme molecule, the molar ratio of such an antibody to such an enzyme in a complex should be 1 or greater. In order to reliably enhance detection sensitivity, such a molar ratio is preferably set in a range from 2 to 5. When Fab' (molecular weight: approximately 50,000) is used as an antibody and when α-amylase (molecular weight: approximately 50,000) is used as am enzyme, the molecular weight of a complex consisting of the antibody and the enzyme is 150,000 daltons or more, and preferably 250,000 to 300,000 daltons, from the viewpoint of high detection sensitivity.

Next, a method for measuring canine TSH (wet process) will be described. First, an antigen contained in an analyte is allowed to come into contact with an enzyme-antibody complex in a solution. At this time, the temperature of the solution is suitably set within a range from approximately 20° C. to 45° C., and the pH thereof is suitably set within a range from approximately pH 4.0 to 8.5. In order to maintain the pH constant, a buffer such as a phosphate buffer or an acetate buffer may be used, as necessary. The contact time of the antigen with the enzyme-antibody complex is not particularly limited, as long as it enables a sufficient reaction of the antigen with the enzyme-antibody complex. For example, when the temperature of the solution is 37° C., the contact time is suitably 20 to 30 minutes. Thereafter, an enzyme substrate is added, and the enzyme activity of the enzyme-antibody complex is measured. If the test antigen is present in the analyte, it can be detected as suppression of the enzyme activity. If a calibration curve is made with a solution containing a known amount of test antigen, the amount of the test antigen in the analyte can be quantified.

Moreover, it may also be possible to carry out only a reaction of an antigen with an enzyme-antibody complex in a solution system and then to perform a dry analysis using the reaction solution after completion of the reaction. Specifically, a dry analytical element comprising a substrate layer containing enzyme substrate of a labeled enzyme may be prepared, and the reaction solution obtained after completion of the immune reaction may be then spotted on the element, thereby measuring enzyme activity.

Furthermore, the monoclonal antibody of the present invention can also be used in a dry analytical element. Specific examples of the configuration of such a dry analytical element include those shown in FIGS. 1 and 2 of Japanese Patent No. 3151080. That is to say, as an example, a detection layer (or a reagent layer) and an immune reaction layer are laminated on a light-transmittable support. The immune reaction layer is composed of a water-penetrable layer, and it contains the enzyme-labeled antibody of the present invention and a non-diffusible substrate used as a substrate of a labeling enzyme. The reagent layer is composed of a water-penetrable layer, and it contains a reagent composition for detecting an enzyme reaction product (a diffusible substance) dispersed and moved from the immune reaction layer. When such an enzyme reaction product is a substance that can be directly detected, such as a colored substance, it is not necessary for the detection layer (or reagent layer) to contain a reagent composition used in detection. In this case, the detection layer (or reagent layer) functions as a detection layer.

An analyte (an antigen) contained in a liquid sample which were supplied by spotting onto the element reacts with an enzyme-labeled antibody via an antigen-antibody bond in the immune reaction layer so as to form a matrix structure. Thus, enzyme activity on a substrate contained in the same immune reaction layer is suppressed. As a result, the amount of the antigen contained in the analyte can be measured based on the amount of an enzyme reaction product detected in the reagent layer (or detection layer).

Moreover, as another example, an enzyme-labeled antibody and an enzyme substrate may be added to different layers. In this case, a water-penetrable substrate layer containing an enzyme substrate is disposed on a reagent layer (or a detection layer), and an immune reaction layer containing an enzyme-labeled antibody is further disposed thereon. In this case, an analyte (an antigen) contained in a liquid sample which were supplied by spotting onto the element reacts with the enzyme-labeled antibody via an antigen-antibody bond in the immune reaction layer to form a matrix structure, so that the analyte becomes substantially immovable. An enzyme-labeled antibody that has not bound to the antigen (or a matrix structure that is small enough not to be captured by a layer structure) moves to the subsequent substrate layer.

In all of the aforementioned embodiments, an enzyme immune reaction can be promoted in the element only by supplying a liquid sample by spotting it onto the element.

In the method for measuring TSH of the present invention, fluorescence intensity can be detected using apparatuses capable of detecting fluorescence intensity, such as a microplate reader or a biosensor for surface plasmon fluorescence (SPF) detection using surface plasmon excitation, although examples of the apparatuses are not limited thereto. Detection of fluorescence intensity is terminated generally within a constant period of time, for example, within several minutes to several hours, after completion of the antigen-antibody reaction. By detecting the degree of formation of the above-described immune complex as fluorescence intensity, the concentration of a detected substance can be quantified based on the relationship between the fluorescence intensity and the concentration of the detected substance. It is to be noted that fluorescence may be measured either by a plate reader measurement or by a flow measurement. The fluorescence detection method involving surface plasmon excitation (SPF method) is able to measure fluorescence intensity with higher sensitivity than that of a fluorescence detection method involving incident light excitation.

The above-described surface plasmon fluorescence (SPF) biosensor can be a sensor, which comprises: a light guide formed from a material for allowing permeation of an excitation light having a certain wavelength; a metal film formed on one surface of this light guide; a light source for generating light beam; an optical system that allows the light beam to pass and enter the light guide at an angle of incidence for generating surface plasmon with respect to the interface between the light guide and the metal film; and a fluorescence-detecting means for detecting fluorescence generated as a result of excitation with an evanescent wave that has been reinforced with the surface plasmon, wherein such a sensor is described, for example, in JP Patent Publication (Kokai) No. 2008-249361 A.

The present invention further relates to a method for measuring canine TSH in a sample, which comprises allowing a sample to come into contact with the aforementioned immunoanalytical reagent for measuring canine TSH of the present invention. The type of a sample is not particularly limited. Examples of such a sample include blood (whole blood, plasma, and serum), lymph, and urine. A preferred example is blood (whole blood, plasma, and serum), more preferred examples are serum and plasma, and a particularly preferred example is serum.

The present invention will be specifically described in the following examples. However, these examples are not intended to limit the scope of the present invention.

EXAMPLES

Example 1

Immunization (1) Preparation of Immunogen 2 mg of Thyroid Stimulating Hormone, Human Pituitary (cat#A81550H), manufactured by BIODESIDG International, was purchased, and it was then used as an immunizing antigen.

(2) Immunization of Mice 2 mg of the immunizing antigen (hTSH) was used. Mice were immunized with the immunizing antigen at an immunizing dose of 50 to 100 μg/mouse for the initial immunization and of 50 μg/mouse for the second and the subsequent immunizations. The immunizing antigen was administered into the subcutis of the dorsal portion of each mouse. For the initial immunization, an emulsion mixed with a Freund's complete adjuvant (FCA) was administered to each mouse. For the second to fourth immunizations, an emulsion mixed with a Freund's incomplete adjuvant (FIA) was administered to each mouse. Immunization was carried out five times at intervals of two weeks. Blood was collected during a week following the third and fourth immunizations, and an antibody titer was measured. An aliquot of the collected blood serum (100 to 200 μL) was used in ELISA measurement. When an increase in the antibody titer was observed, the fifth immunization was defined as a final immunization. For the final immunization, the antigen A was diluted with PBS(−), and was then administered into the abdominal cavity of each mouse. Three days after the final immunization, the spleen was excised from each mouse.

(1) Animal: BALB/c mice, female, 6- to 7-week-old
(2) Number of mice: 3
(3) Immunizing dose: 50-100 μg/mouse/single dose
(4) Site immunized: administration into caudal vein or abdominal cavity
(5) Measurement of antibody titer: ELISA The spleen was excised from mice (1 to 3 mice) that had been selected as a result of the measurement of the antibody titer, and cell fusion was then performed.

Example 2

Preparation of Hybridoma

Cell fusion was performed by mixing the spleen cells excised from the immunized mice with myeloma cells.
Fusion method: PEG method
Cells used: spleen cells three days after the final immunization
Myeloma: P3-X63-Ag8-U1
Cell ratio of splenic cells:myeloma cells=5 to 10:1
Cell seeding: Spleen cells were seeded at a density of 0.5 to $1.0 \times 10^5$ cells/well on a 96-well plate.
Medium used: RPMI-1640+10% FBS+HAT (In some cases, HCF or IL-6 may be further added thereto.)

Example 3

Evaluation of Reactivity of Antibodies with hTSH Antigen First Screening of Monoclonal Antibody (Screening after Cell Fusion)

An antigen used in measurement was diluted with PBS(−) to a concentration of 500 ng/mL, and was then immobilized. A culture supernatant of hybridoma, which had been proliferated by selective culture in a HAT medium, was screened by ELISA. An anti-mouse IgG HRP-labeled antibody was used as a secondary antibody. Hybridomas that were positive in the screening were cultured in a 24-well plate, and thereafter, 1 mL each of culture supernatant was used in evaluation. Based on the selective test results by SPR, cloning wells were selected. In the SPR, CM5 was used as a sensor chip, and hTSH was immobilized at a level of RU=approximately 200 according to an amine coupling method.

The concentration of each antibody in the culture supernatant was quantified with CaptureAb (immobilized at a level of RU=approximately 2000). Using the obtained values, a comparison was made in terms of the binding ability of each antibody to the hTSH antigen. The results are shown in FIG. 1.

Normalization of antibody concentration: ΔRU at hTSH/ΔRU at Capture×100

The concentrations of the antibodies were normalized, and thereafter, a comparison was made in terms of the binding ability of each antibody to the hTSH antigen. As a result, a well having high binding ability was identified.

Example 4

Evaluation of Reactivity of Antibodies with Canine TSH (cTSH)

When the amino acid sequence of human-derived TSH is compared with the amino acid sequence of canine-derived TSH, it is found that there is a common sequence portion shared by canine and human. Accordingly, there is possibility that an antibody reacting with both human TSH (hTSH) and cTSH can be obtained. Thus, using a cTSH antigen, screening was carried out as in the case of hTSH.

Conditions for SPR measurement were determined as follows. Ager completion of the cell fusion, 35 wells of ELISA positive samples (culture supernatants) were flown over the chip. HBS-EP buffer, Flow: 30 µl/min, contact time: 5 min, Flow: 5 min, Wash: 5 min (Gly, pH 1.5)

cTSH antigen: manufactured by *Scrips* (100 µg), Specific activity: approximately 5%

Chip: CM5

Fc1: baseline

Fc2: cTSH immobilization (RU=approximately 2000 to 4000)

Figure 2:
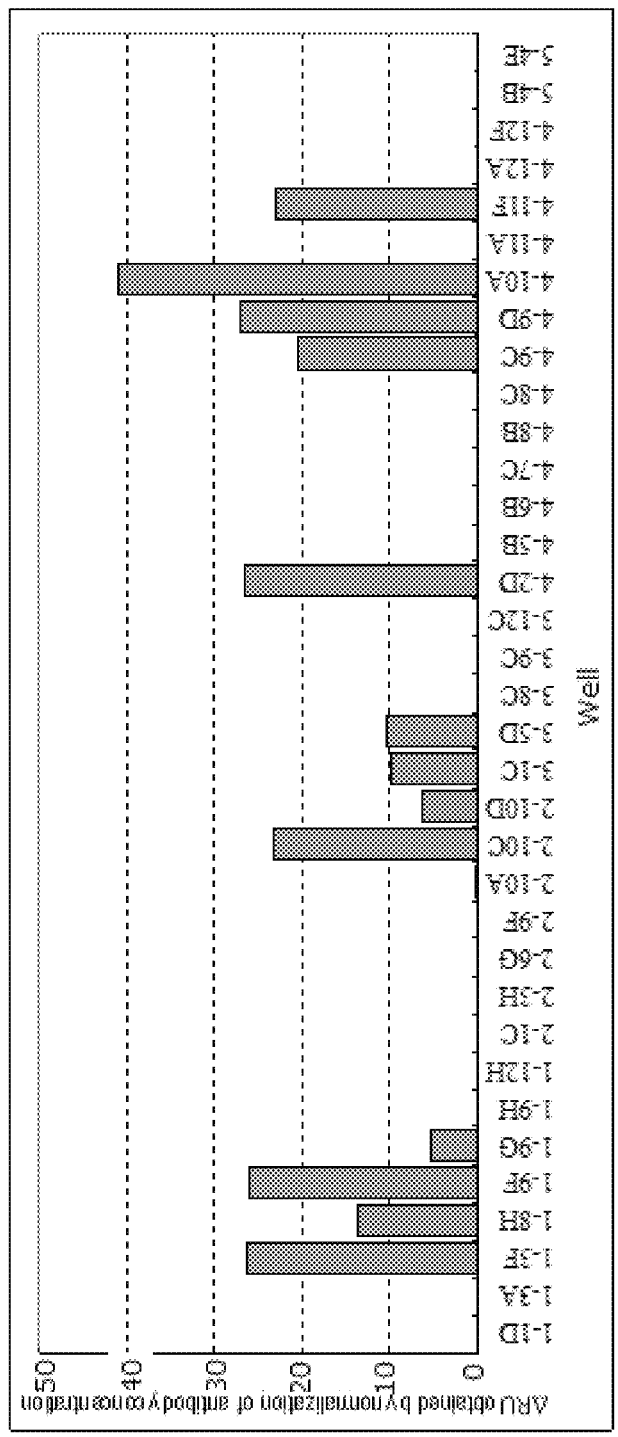
FIG. 2 shows the reactivity of the obtained antibody with a canine TSH antigen.

Screening was performed on the 35 wells in the above-described evaluation system. As in the case of hTSH, the values obtained by normalization of antibody concentrations (value of cTSH/capture AB*100) were summarized in a bar chart. The results summarized in such a bar chart are shown in FIG. 2.

13 out of the 35 wells reacted with the cTSH antigen. The top 10 wells were subjected to cloning and the establishment of hybridomas.

The screening results obtained using hTSH and cTSH antigens are summarized in the following Table 1 (regarding the top 10 wells).

TABLE 1

| Wells reacted with hTSH | Wells reacted with cTSH | Wells reacted with both TSHs |
|---|---|---|
| 1-1D | 1-8H | |
| 1-3F | 1-3F | ◯ |
| 1-9F | 1-9F | ◯ |
| 2-10C | 2-10C | ◯ |
| 3-1C | 3-5D | |
| 4-8B | 4-2D | |
| 4-9D | 4-9D | ◯ |
| 4-10A | 4-10A | ◯ |
| 4-11F | 4-11F | ◯ |
| 5-4E | 4-9C | |

6 out of the top 10 wells reacted with both human TSH and canine TSR

Example 5

Second Screening of Monoclonal Antibodies (Screening after Limiting Dilution)

Figure 3:
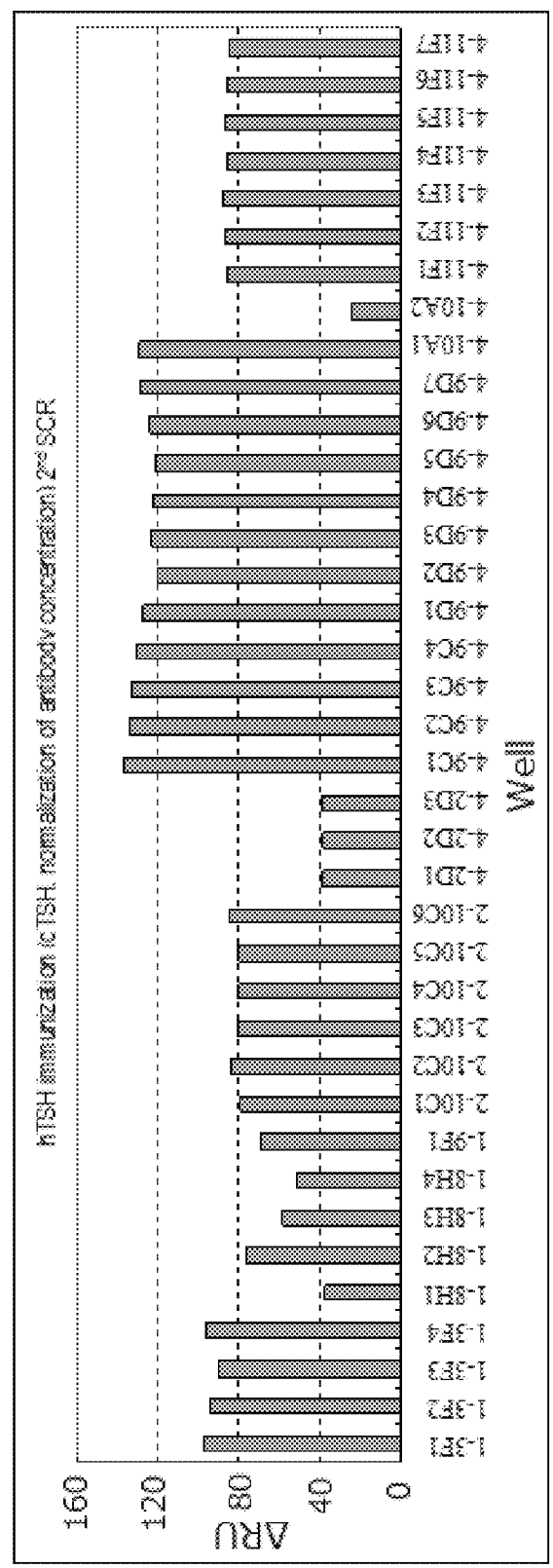
FIG. 3 shows the screening results of the obtained antibody after limiting dilution (the results of evaluation of the reactivity of the obtained antibody with a cTSH antigen).
Figure 4:
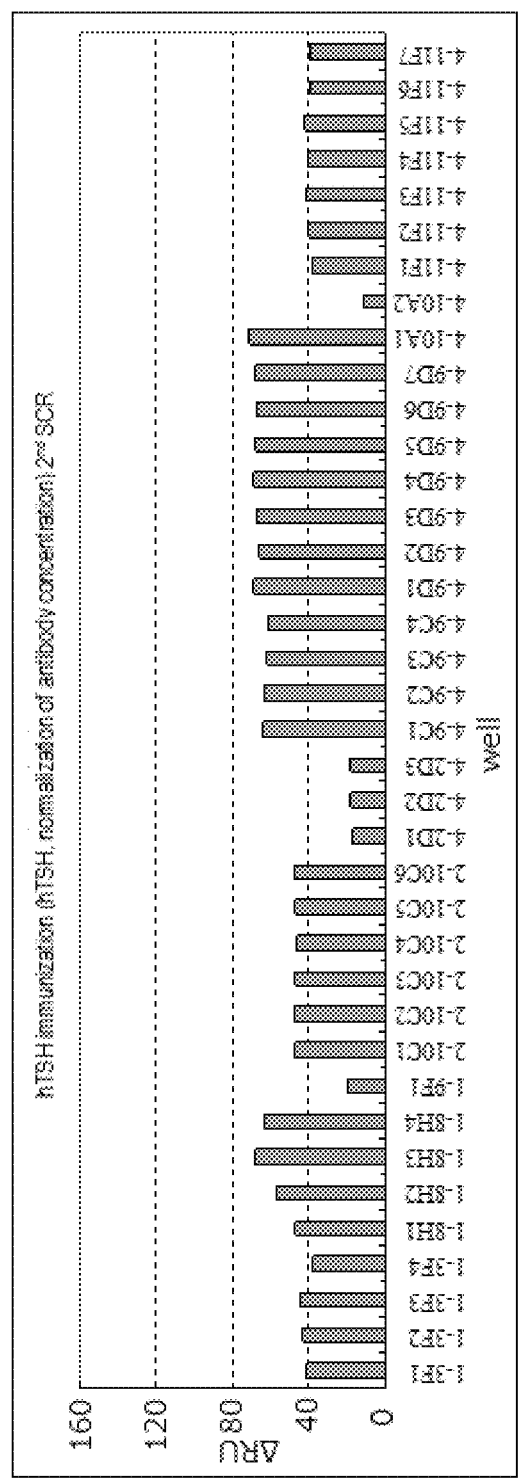
FIG. 4 shows the screening results of the obtained antibody after limiting dilution (the results of evaluation of the reactivity of the obtained antibody with a hTSH antigen).
Figure 5:
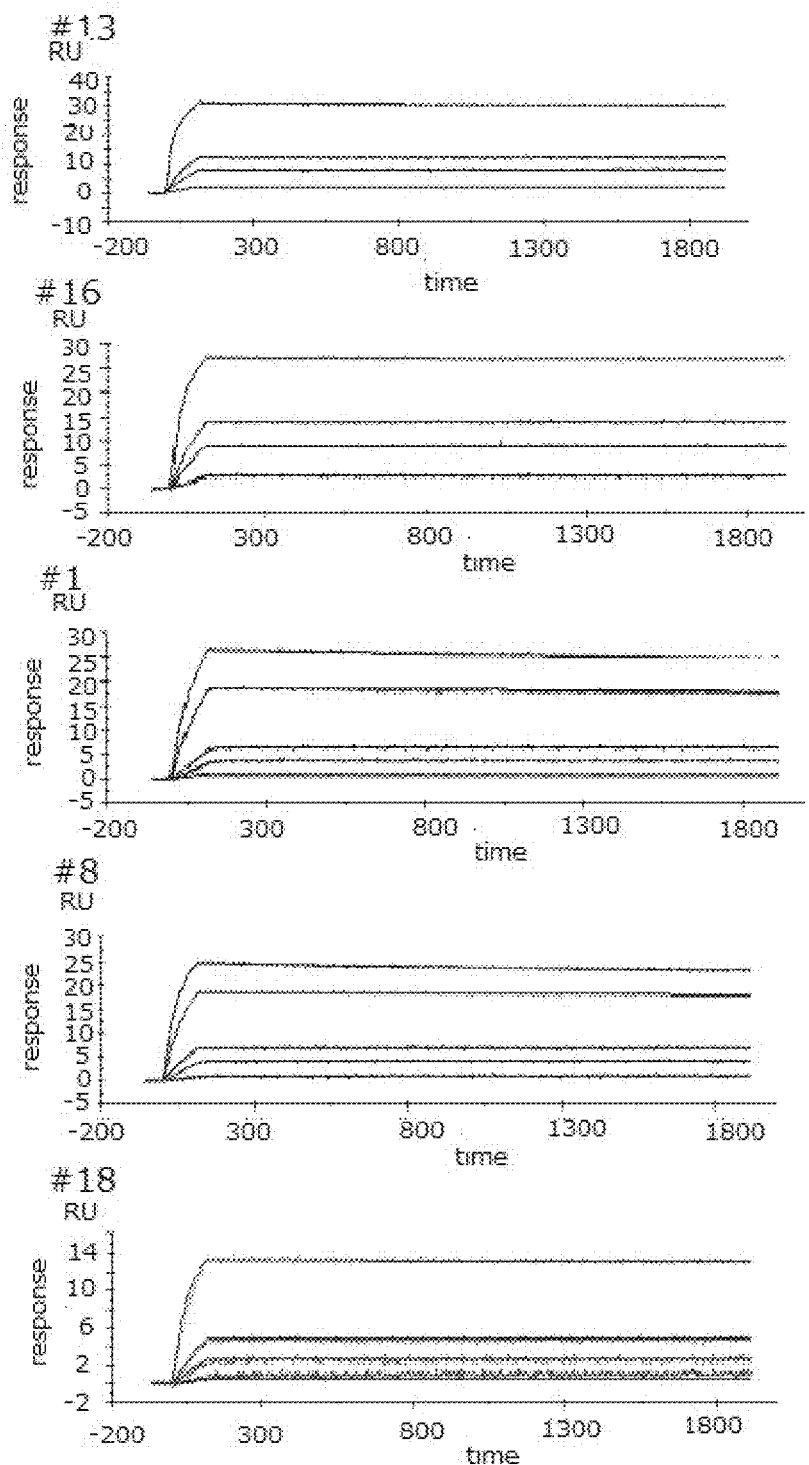
FIG. 5 is a sensorgram showing the kinetics analysis of the antibody of the present invention.

Monoclonal antibodies were subjected to a second screening (which was a screening conducted after completion of limiting dilution) in the same manners as those of Examples 3 and 4. The results are shown in FIG. 3 and FIG. 4. Subclasses were determined using Isotyping Kit (manufactured by Roche). In addition, several superior strains having high SPR signals were selected in the each of the parent clones, and they were then used in the production of frozen vials. The results are shown in the following Table 2.

TABLE 2

Summary of Final Clone Selection Results

| Parent clone | Strain name | Subclass |
|---|---|---|
| 1-3F | 1-3F2 | IgG1 |
|  | 1-3F4 | IgG1 |
| 1-8H | 1-8H1 | IgG2b |
|  | 1-8H2 | IgG2b |
|  | 1-8H3 | IgG2b |
|  | 1-8H4 | IgG2b |
| 1-9F | 1-9F1 | IgG2a |
| 2-10C | 2-10C2 | IgG1 |
|  | 2-10C6 | IgG1 |
| 4-2D | 4-2D1 | IgG1 |
|  | 4-2D3 | IgG1 |
| 4-9C | 4-9C1 | IgG1 + IgM |
|  | 4-9C2 | IgG1 |
| 4-9D | 4-9D1 | IgG1 |
|  | 4-9D7 | IgG1 |
| 4-10A | 4-10A1 | IgG1 |
|  | 4-10A2 | IgG1 |
| 4-11F | 4-11F2 | IgG1 |
|  | 4-11F3 | IgG1 |
|  | 4-11F5 | IgG1 |

Example 6

Production of Antibodies by Mouse Ascites Method

SPR screening was conducted through the final clones. A mouse ascites method (wherein two mice were used) was applied to superior clones having high signals, which had been selected as a result of the SPR screening, so as to produce antibodies. The below-mentioned amounts of antibodies were produced.

TABLE 3

Amounts of Antibodies Produced

| Clone name (Strain name) | Number used during screening (Number in Table 2) | Subclass | Amount produced |
|---|---|---|---|
| TSH #1 (1-3F2) | 1-3F2 | IgG1 | 5.0 mg |
| TSH #8 (2-10C2) | 2-10C2 | IgG1 | 14.7 mg |
| TSH #13 (4-9C2) | 4-9C2 | IgG1 | 18.4 mg |
| TSH #16 (4-10A1) | 4-10A1 | IgG1 | 28.5 mg |
| TSH #18 (4-11F2) | 4-11F2 | IgG1 | 19.6 mg |

Note:
Hereafter, clones may be indicated with # numbers for simplification.

The hybridomas, which produce the above-described monoclonal antibodies TSH #1 (1-3F2), TSH #8 (2-10C2), TSH #13 (4-9C2), and TSH #18 (4-11F2), were deposited with the NITE International Patent Organism Depositary (IPOD), the National Institute of Advanced Industrial Science and Technology, an Independent Administrative Institution under the Ministry of Economy, Trade and Industry (AIST, Tsukuba Central 6, Higashi 1-1-1, Tsukuba, Ibaraki, Japan), under the accession numbers as described below, on Mar. 1, 2011. The deposition of the hybridoma TSH #1 (1-3F2) under the Accession No. FERM P-22073 was transferred to an International Deposit under the Budapest Treaty under the Accession No. FERM BP-11489 on Jun. 11, 2012.

The hybridoma, which produces the above-described monoclonal antibody TSH #16 (4-10A1), was deposited with the NITE International Patent Organism Depositary (IPOD), the National Institute of Advanced Industrial Science and Technology, an Independent Administrative Institution under the Ministry of Economy, Trade and Industry (AIST, Tsukuba Central 6, Higashi 1-1-1, Tsukuba, Ibaraki, Japan); under the accession number as described below, on Jul. 22, 2011. The deposition of the hybridoma TSH #16 (4-10A1) under the Accession No. FERM P-22154 was transferred to an International Deposit under the Budapest Treaty under the Accession No. FERM BP-11490 on Jun. 11, 2012.

TABLE 4

Accession Numbers of Hybridomas

| Hybridoma clone name (Strain name) | Accession No. |
|---|---|
| TSH #1 (1-3F2) | FERM BP-11489 (from FERM P-22073) |
| TSH #8 (2-10C2) | FERM P-22074 |
| TSH #13 (4-9C2) | FERM P-22075 |
| TSH #16 (4-10A1) | FERM BP-11490 (from FERM P-22154) |
| TSH #18 (4-11F2) | FERM P-22077 |

Example 7

Kinetics Analysis of TSH Antibodies (Biacore, T-100)

The five types of antibodies (#1, #8, #18, #13, and #16) as shown in the above Table 4 were subjected to kinetics analysis.
Apparatus: Biacore T100
(Measurement Conditions)
  Contact time: 120 s
  Flow rate: 60 µL/min
  Dissociation time: 1800 s
  Regeneration: 10 mM Gly pH 1.5, Contact time: 300 s, Flow rate: 30 µL/min
  Chip: CM5, hTSH (Calbiochem), immobilized at RU=12
The measurement results are shown in the following Table 5.

TABLE 5

Kinetics Analysis of Antibodies

| Immunogen | Clone | $k_a$ (M$^{-1}\cdot$s$^{-1}$) | $k_d$ (s$^{-1}$) | $K_D$ (M) |
|---|---|---|---|---|
| hTSH | #13 | $6.02 \times 10^5$ | $3.02 \times 10^{-5}$ | $5.0 \times 10^{-11}$ |
| hTSH | #16 | $6.14 \times 10^5$ | $1.30 \times 10^{-5}$ | $2.1 \times 10^{-11}$ |
| hTSH | #1 | $9.30 \times 10^5$ | $2.08 \times 10^{-4}$ | $2.23 \times 10^{-10}$ |
| hTSH | #8 | $1.07 \times 10^6$ | $9.97 \times 10^{-5}$ | $9.28 \times 10^{-11}$ |
| hTSH | #18 | $1.29 \times 10^5$ | $5.78 \times 10^{-5}$ | $4.48 \times 10^{-10}$ |

Example 8

Evaluation of Antibodies TSH #13 (4-9C2) and TSH #16 (4-10A1) in SPF Detection

The antibody TSH #13 (4-9C2) or TSH #16 (4-10A1), which had been bound to fluorescent particles, and a commercially available anti-TSH antibody, were immobilized on a substrate, and thereafter, an SPF assay was carried out by the following procedures.
Production of Antibody-Bound Fluorescent Latex Particles A solution (250 µL) of 2 mg/mL TSH monoclonal antibody (the antibody TSH #13 (4-9C2) or TSH #16 (4-10A1)) and 50 mM MES buffer (pH 6.0) were added to 250 µL of a 2% (solid concentration) fluorescent latex particle aqueous solution, and the obtained mixture was then stirred at room temperature for 15 minutes. Thereafter, 5 µL of a 10 mg/mL WSC (product number: 01-62-0011, Wako Pure Chemical Industries) aqueous solution was added to the reaction solution, and the obtained mixture was then stirred at room temperature for 2 hours. Subsequently, 25 µL of a 2 mol/L glycine aqueous solution was added to the reaction solution, and the obtained mixture was then stirred for 30 minutes. Thereafter, fluorescent latex particles were precipitated by performing centrifugation on the reaction solution (15,000 rpm, 4° C., 15 minutes). The supernatant was removed, and 500 µL of a PBS solution (pH 7.4) was then added to the precipitate. Then, fluorescent latex particles were re-dispersed using an ultrasonic washer. The resultant was further subjected to centrifugation (15,000 rpm, 4° C., 15 minutes) to remove the supernatant, and 500 µL of a PBS (pH 7.4) solution containing 1% BSA was then added thereto, so as to re-disperse fluorescent latex particles, thereby obtaining a solution of 1% (w/v) TSH antibody-bound fluorescent latex particles.
Description Regarding Analysis of SPF Immunoassay (Assay System Using TSH Antigen)
Description Regarding Production of Cartridge There was used a chip, in which a gold film had been deposited via evaporation on a substrate, using methyl polymethacrylate as a base. Using this chip, an antibody solution was spotted on the gold film, so as to immobilize the antibody thereon. Thereafter, using antibody-labeling fluorescent particles, an immunoassay was carried out by the following procedures.

Before a top plate was equipped in the flow channel of a sensor chip, 100 µL of a 150 mM sodium chloride solution of a TSH monoclonal antibody (an existing commercially available anti-TSH antibody), which had been adjusted to 10 µg/mL, was added to a measurement area of the sensor chip. It was left at rest at room temperature for 1 hour. Thereafter, the antibody solution was removed, and the area was then washed with a previously prepared washing buffer (PBS (pH 7.4) containing 0.05% (w/v) Tween-20) (300 µL/once, three times). After completion of the washing treatment, in order to block an unadsorbed portion of the antibody, 300 µL of PBS (pH 7.4) containing 1% casein was added, and the chip was then left at rest at room temperature for 1 hour. Thereafter, the reaction solution was washed with the aforementioned washing buffer, and 300 µL of Immunoassay Stabilizer (manufactured by ABI) was then added as a stabilizer to each well. The resultant was left at room temperature for 30 minutes. Thereafter, the solution was removed, and water content was completely eliminated in a dryer. After completion of the treatment of binding the TSH antibody, the flow channel of the sensor chip was enclosed with a covering material, so as to produce a flow-channel sensor chip. In order to enclose the flow channel, a method such as ultrasonic welding can be used.

Description of Antigen Concentration

TSH antigens were each added in concentrations of 15 µM, 48 µM and 187 µM to canine plasma, so as to prepare sample solutions.

Description of Measurement System

5 µL of the 1% anti-TSH antibody-bound fluorescently labeling substance solution, which had been prepared by the above-described procedures, was added to each of the sample solutions (500 µL each), so as to prepare reaction solutions. Using a sample cell, fluorescent signals from the measurement area were measured at a plurality of different time points, while supplying the reaction solution onto the measurement area. Fluorescent signals were measured by irradiating a region in which a complex (antibody-antigen-antibody) was formed on the gold film, with a near-infrared laser from the side to which the antibody did not bind, so as to generate an evanescent wave. Since such an evanescent wave reaches only around the gold film, it mainly excites a labeling substance contained in the above-described sandwich complex, and as a result, fluorescence is emitted. The fluorescence was detected using a photo diode. During this operation, a pump was connected with an air vent of the sample cell, and suction was then performed with the pump so that the flow rate could be constant (linear velocity: 1.4 mm/s). While supplying 300 µL of the reaction solution to the measurement area, measurement was carried out. Reaction conditions: first reaction for 10 minutes; flow rate of 10 µL/min; flow time of 5 minutes; and washing time of 5 minutes.

Figure 6:
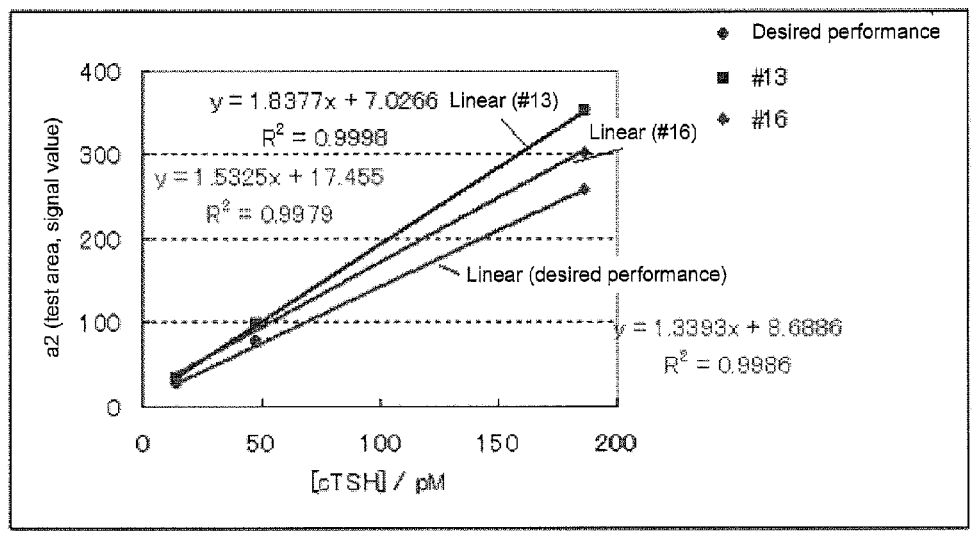
FIG. 6 shows the results obtained by evaluating the antibodies of the present invention TSH #13 (4-9C2) and TSH #16 (4-10A1) by SPF detection.

The results of the above-described measurement are shown in FIG. 6. The results shown in FIG. 6 are summarized in Table 6 as shown below. From the results shown in FIG. 6 and Table 6, it was demonstrated that, when the antibodies of the present invention TSH #13 (4-9C2) and TSH #16 (4-10A1), which have been bound to fluorescent particles, are used in SPF detection, desired performance can be achieved.

TABLE 6

Calibration Curves of Antibodies

| Antibody | Calibration curve |
| --- | --- |
| Desired performance | Y = 1.3393x + 8.6886 |
| TSH #13 (4-9C2) | Y = 1.8377x + 7.0266 |
| TSH #16 (4-10A1) | Y = 1.5325x + 17.455 |

Example 9

Screening for Substrate Side Antibody Usable as Pair with Antibody TSH #13 (4-9C2) or TSH #16 (4-10A1)

A substrate side antibody, which can be used when either the antibody TSH #13 (4-9C2) or TSH #16 (4-10A1) is used as a fluorescently labeled antibody, was screened by the following procedures. It is to be noted that the following antibodies were used as candidates for such substrate side antibodies.

TABLE 7

Antibodies on Substrate Side

| Clone name (Strain name) | Number used during screening (Number in Table 2) |
| --- | --- |
| TSH #1 (1-3F2) | 1-3F2 |
| TSH #4 (1-8H2) | 1-8H2 |
| TSH #7 (1-9F1) | 1-9F1 |
| TSH #8 (2-10C2) | 2-10C2 |
| TSH #10 (4-2D1) | 4-2D1 |
| TSH #13 (4-9C2) | 4-9C2 |
| TSH #14 (4-9D1) | 4-9D1 |
| TSH #16 (4-10A1) | 4-10A1 |
| TSH #18 (4-11F2) | 4-11F2 |

Apparatus: Biacore T100
(Measurement Conditions)
  Contact time: 120 s
  Flow rate: 30 µL/min
  Dissociation time: 120 s
  Regeneration: 10 mM. Gly pH 1.5, Contact time: 300 s, Flow rate: 30 µL/min
  Chip: CM5, cTSH (Scrips), immobilized at RU=4000
  The antibody SH #13 (4-9C2) or TSH #16 (4-10A1) (50 µg/ml) was flown over a cTSH-immobilized chip. Thereafter, the candidates (5 µg/ml) for substrate side antibody as shown in the above Table 7 were each flown over the chip, so as to obtain a sensorgram. The bound amount obtained when the antibody TSH #13 (4-9C2) or TSH #16 (4-10A1) of Table 7 was flown over the chip is defined as ΔRU1, and the bound amount when the candidate for substrate side antibody was flown over the chip is defined as ΔRU2. The values obtained by flowing individual antibodies over the chip are summarized in a bar chart. The results summarized in such bar charts are shown in FIG. 7 and FIG. 8.

Figure 7:
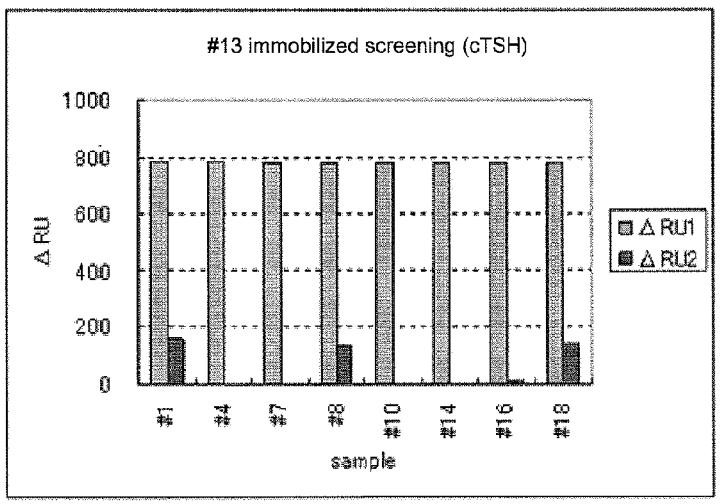
FIG. 7 shows the results obtained by screening for an antibody on a substrate side, which can be used as a pair with the antibody TSH #13 (4-9C2).
Figure 8:
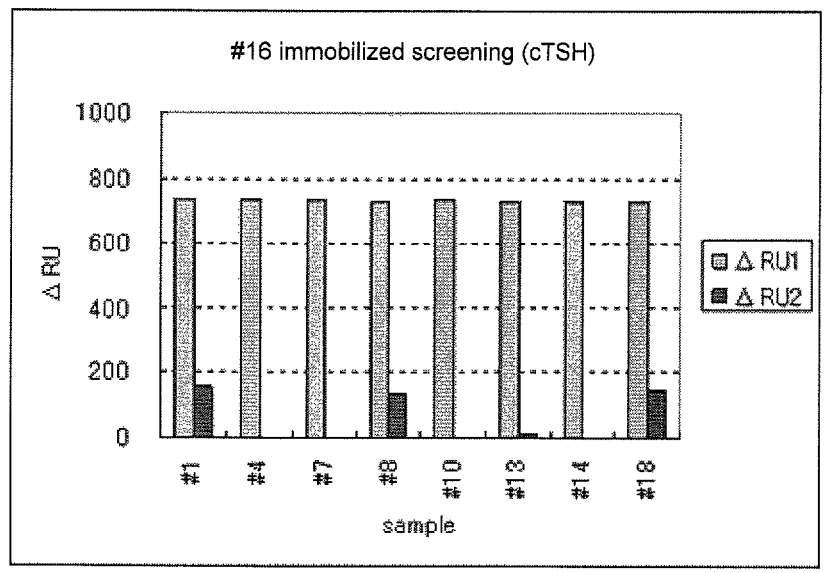
FIG. 8 shows the results obtained by screening for an antibody on a substrate side, which can be used as a pair with the antibody TSH #16 (4-10A1).

FIG. 7 shows the measurement results obtained in the case of using the antibody TSH #13 (4-9C2), whereas FIG. 8 shows the measurement results obtained in the case of using the antibody TSH #16 (4-10A1). As is clear from the results shown in FIG. 7 and FIG. 8, in both cases of the antibody TSH #13 (4-9C2) and the antibody TSH #16 (4-10A1), signals sufficient for achieving desired performance could be obtained when the antibody TSH #1 (1-3F2), the antibody TSH #8 (2-10C2) or the antibody TSH #18 (4-11F2) was used.

The invention claimed is:

1. An isolated monoclonal antibody produced by a hybridoma having Accession No. FERM BP-11490.

2. A hybridoma having Accession No. FERM BP-11490.

3. An immunoanalytical reagent which comprises the antibody according to claim 1 or a functional fragment thereof.

4. An immunoanalytical reagent which comprises the antibody according to claim 1 or a functional fragment thereof, wherein the antibody or a functional fragment thereof is labeled with latex particles containing a dye or a fluorescent dye.

5. An immunoanalytical reagent which comprises the antibody according to claim 1 or a functional fragment thereof, wherein the antibody or the functional fragment thereof is labeled with an enzyme.

6. An immunoanalytical reagent consisting of a combination of a labeled antibody prepared by labeling a monoclonal antibody produced by a hybridoma having Accession No. FERM BP-11490 with latex particles containing a dye or a fluorescent dye, and a monoclonal antibody produced by a hybridoma having Accession No. FERM BP-11489.

7. The immunoanalytical reagent according to claim 3, which is used in a measurement of canine thyroid stimulating hormone (TSH).

8. A method for measuring thyroid stimulating hormone (TSH) in a sample, which comprises contacting the sample with the immunoanalytical reagent according to claim 3.

* * * * *